United States Patent
Ramasamy et al.

(10) Patent No.: US 10,221,119 B2
(45) Date of Patent: Mar. 5, 2019

(54) CONVERSION OF ETHANOL TO $C_5+$ KETONES IN SINGLE CATALYST BED

(71) Applicant: BATTELLE MEMORIAL INSTITUTE, Richland, WA (US)

(72) Inventors: Karthikeyan Kallupalayam Ramasamy, West Richland, WA (US); Michel J. Gray, Kennewick, WA (US); Carlos A. Alvarez-Vasco, Itagui (CO); Mond F. Guo, Richland, WA (US); Senthil Subramaniam, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 15/871,773

(22) Filed: Jan. 15, 2018

(65) Prior Publication Data

US 2018/0215692 A1 Aug. 2, 2018

Related U.S. Application Data

(60) Provisional application No. 62/452,143, filed on Jan. 30, 2017.

(51) Int. Cl.
| | | |
|---|---|---|
| *C07C 45/45* | (2006.01) | |
| *B01J 23/72* | (2006.01) | |
| *B01J 23/80* | (2006.01) | |

(52) U.S. Cl.
CPC .............. *C07C 45/45* (2013.01); *B01J 23/72* (2013.01); *B01J 23/80* (2013.01)

(58) Field of Classification Search
CPC ...................................................... C07C 45/45
See application file for complete search history.

(56) References Cited

PUBLICATIONS

Schuyten et al. A Novel Combustion Synthesis Preparation of CuO/ZnO/Zr2O2/Pd for Oxidative Hydrogen Production from Methanol. Catalyst Letters, vol. 121, 189-198. (Year: 2008).*
Anbarasan, P., et al., Integration of chemical catalysis with extractive fermentation to produce fuels, Nature, 491, 7423, 2012, 235-239.
Goulas, K. A., et al., ABE Condensation over Monometallic Catalysts: Catalyst Characterization and Kinetics, ChemCatChem, 9, 2017, 677-684.
Gurbuz, E. I., et al., Dual-bed catalyst system for C-C coupling of biomass-derived oxygenated hydrocarbons to fuel-grade compounds, Green Chemistry, 12, 2, 2010, 223-227.
Kamimura, Y., et al., Synthesis of e-pentanone from 1-propanol over CeO2—Fe2O3 catalysts, Applied Catalysis A: General , 252, 2003, 399-410.
Martinez-Ortiz, M. d-J., et al., The "one-pot" synthesis of 4-methyl-2-pentanone (methyl isobutyl ketone) from acetone over PdCu catalysts prepared from layered double hydroxides, Journal of Molecular Catalysis A: Chemical, 201, 2003, 199-210.
Onyestyak, G., et al., Upgraded biofuel from alcohol-acetone feedstocks over a two-stage flow-through catalytic system, Catalysis Science & Technology, 6, 2016, 4516-4524.
Sreekumar, S., et al., Chemocatalytic Upgrading of Tailored Fermentation Products Toward Biodiesel, ChemSusChem, 7, 2014, 2445-2448.

* cited by examiner

*Primary Examiner* — Sikarl A Witherspoon
(74) *Attorney, Agent, or Firm* — Derek H. Maughan

(57) ABSTRACT

Methods, systems and catalysts for converting an alcohol containing feedstock to an upgraded material in a single catalyst bed wherein a feedstock is fed to a catalyst under preselected conditions to obtain an intermediate; and condensing the intermediate through an aldol condensation reaction to yield a product containing an upgraded material. In one instance the feedstock includes ethanol, the catalyst is a mixed metal oxide catalyst and the upgraded material is typically a $C_5+$ ketone(s) or alcohol(s), such as 2-pentanone, 2-heptanone, 4-heptanone and 2-nonanone.

14 Claims, 5 Drawing Sheets

| Notes | Mixed Oxide (ratio) | Metal (wt%) | Temperature (°C) | Ethanol Conversion (%) | Selectivity % | | | | | | | | |
|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature | ZrZn(2:1) | Pd(0.05) | 340 | 93.59% | 11.46% | 29.64% | 10.63% | 2.76% | 1.04% | 0.21% | 8.04% | 10.72% | 7.78% | 24.20% | 2.52% |
| | ZrZn(2:1) | Pd(0.05) | 355 | 98.81% | 13.93% | 29.05% | 16.82% | 5.66% | 1.66% | 0.50% | 12.32% | 7.79% | 5.05% | 3.51% | 3.71% |
| | ZrZn(2:1) | Pd(0.05) | 370 | 99.51% | 10.92% | 29.04% | 18.42% | 6.94% | 3.64% | 0.70% | 14.10% | 3.07% | 1.21% | 0.43% | 11.53% |

Fig. 3A

| Notes | Mixed Oxide (ratio) | Metal (wt%) | Temperature (°C) | Ethanol Conversion (%) | Selectivity % | | | | | | | | |
|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature + Potassium | ZrZn(2:1) | Pd(0.05)+1%K | 340 | 95.89% | 13.08% | 27.53% | 12.96% | 3.01% | 0.93% | 0.20% | 9.91% | 9.94% | 6.57% | 13.10% | 2.76% |
| | ZrZn(2:1) | Pd(0.05)+1%K | 355 | 99.42% | 13.06% | 31.60% | 18.61% | 5.59% | 1.42% | 0.38% | 10.93% | 7.09% | 4.53% | 1.16% | 5.62% |
| | ZrZn(2:1) | Pd(0.05)+1%K | 370 | 99.02% | 12.49% | 29.68% | 17.32% | 6.23% | 3.04% | 0.59% | 14.20% | 3.99% | 1.88% | 0.79% | 9.78% |

Fig. 3B

| Notes | Mixed Oxide (ratio) | Metal (wt%) | Temperature (°C) | Ethanol Conversion (%) | Selectivity % | | | | | | | | |
|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature | ZrZn(2:1) | Pd(0.1) | 340 | 95.86% | 10.38% | 24.02% | 13.73% | 3.91% | 1.27% | 0.33% | 9.29% | 7.36% | 10.55% | 16.38% | 2.78% |
| | ZrZn(2:1) | Pd(0.1) | 355 | 98.93% | 10.44% | 28.88% | 19.75% | 7.73% | 2.05% | 0.62% | 12.39% | 6.26% | 4.86% | 1.70% | 5.32% |
| | ZrZn(2:1) | Pd(0.1) | 370 | 99.52% | 7.64% | 25.13% | 21.81% | 7.49% | 5.13% | 1.05% | 13.83% | 2.62% | 0.67% | 0.35% | 14.08% |

Fig. 3C

| Notes | Mixed Oxide (ratio) | Metal (wt%) | Temperature (°C) | Ethanol Conversion (%) | Selectivity % | | | | | | | | |
|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 2 to 1 ratio at different temperature + Potassium | ZrZn(2:1) | Pd(0.1)+1%K | 340 | 95.43% | 9.18% | 26.95% | 15.58% | 3.88% | 1.02% | 0.30% | 10.08% | 7.55% | 8.76% | 13.61% | 3.08% |
| | ZrZn(2:1) | Pd(0.1)+1%K | 355 | 98.79% | 11.26% | 31.34% | 18.95% | 5.92% | 1.47% | 0.36% | 13.20% | 6.21% | 3.85% | 1.48% | 5.96% |
| | ZrZn(2:1) | Pd(0.1)+1%K | 370 | 99.54% | 10.37% | 28.51% | 20.44% | 6.54% | 3.55% | 0.54% | 13.92% | 2.84% | 0.71% | 1.06% | 11.52% |

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 1 to 2 ratio at different temperature | Zr:Zn(1:2) | Pd(0.1) | 340 | 91.66 | 7.22% | 18.27% | 8.88% | 3.37% | 0.78% | 0.26% | 7.20% | 8.13% | 11.44% | 31.61% | 2.85% |
| | Zr:Zn(1:2) | Pd(0.1) | 355 | 97.2 | 9.21% | 26.45% | 15.91% | 6.22% | 1.73% | 0.53% | 11.16% | 7.43% | 9.42% | 8.99% | 2.95% |
| | Zr:Zn(1:2) | Pd(0.1) | 370 | 99.78 | 6.63% | 29.86% | 19.24% | 8.94% | 5.18% | 0.80% | 11.88% | 3.60% | 4.67% | 0.65% | 6.55% |

Fig. 3F

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Zr:Zn with 1 to 1 ratio at different temperature | Zr:Zn(1:1) | Pd(0.1) | 340 | 84.27 | 5.21% | 11.18% | 6.58% | 1.65% | 0.67% | 0.05% | 4.47% | 7.45% | 12.38% | 47.81% | 2.55% |
| | Zr:Zn(1:1) | Pd(0.1) | 355 | 91.95 | 8.17% | 19.50% | 11.23% | 3.04% | 1.18% | 0.16% | 8.89% | 7.83% | 10.03% | 25.96% | 3.72% |
| | Zr:Zn(1:1) | Pd(0.1) | 370 | 97.7 | 11.04% | 26.49% | 13.42% | 6.41% | 2.83% | 0.63% | 13.56% | 5.63% | 5.65% | 9.41% | 5.95% |

Fig. 3G

| Notes | Mixed Oxide (ratio) | Metal (wt%) | Temperature (°C) | Ethanol Conversion (%) | Selectivity % | | | | | | | | | |
|---|---|---|---|---|---|---|---|---|---|---|---|---|---|---|
| | | | | | Acetone | Pentanone | Heptanone | Nonanone | Undecanone | Tridecanone | CO2 | Alcohols | Aldehydes | Esters | Others |
| Different metal impregnations | Zr:Zn(2:1) | | 370 | 60.46 | 6.62% | 2.18% | 1.21% | 0.16% | 0.00% | 0.00% | 5.63% | 2.83% | 8.13% | 34.15% | 39.09% |
| | Zr:Zn(2:1) | Cu(1) | 370 | 95.08 | 12.95% | 24.55% | 12.60% | 4.57% | 0.86% | 0.19% | 11.79% | 7.31% | 7.93% | 8.93% | 8.32% |
| | Zr:Zn(2:1) | Ag(0.5) | 370 | 99.71 | 16.33% | 22.97% | 7.75% | 2.23% | 0.69% | 0.80% | 19.25% | 2.34% | 0.56% | 0.17% | 26.98% |
| | Zr:Zn(2:1) | Pt(0.1) | 370 | 99.3 | 8.72% | 24.74% | 12.20% | 4.78% | 1.41% | 0.44% | 12.18% | 3.39% | 2.65% | 2.59% | 26.90% |
| | Zr:Zn(2:1) | Pd(0.05) | 370 | 99.91 | 9.53% | 27.65% | 16.09% | 7.39% | 5.14% | 2.28% | 14.25% | 3.19% | 1.88% | 1.88% | 10.73% |
| | Zr | Pd(0.1) | 370 | 56.47 | 1.86% | 5.82% | 1.02% | 0.07% | 0.00% | 0.00% | 3.28% | 17.84% | 1.08% | 2.24% | 66.80% |

CONVERSION OF ETHANOL TO C$_5$+ KETONES IN SINGLE CATALYST BED

PRIORITY

This application claims priority from a provisional patent application entitled CONVERSION OF ETHANOL TO C5+ KETONES IN SINGLE CATALYST BED filed Jan. 30, 2017 U.S. Patent Application No. 62/452,143, the contents of which are hereby incorporated by reference in their entirety.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

BACKGROUND OF THE INVENTION

Field of the Invention

The invention generally relates to chemical and chemical synthesis and more particularly to systems and methodologies for upgrading and modifying alcohols such as ethanol to higher products such as ketones.

Background Information

Ethanol is a commercially produced chemical with domestic production near 15 billion gallons. Despite its availability, broader utilization of ethanol based products has been limited due to a variety of factors. Among these factors is the so called "blend wall" whereby the inclusion of ethanol is limited in various applications because of concerns about negative associated complications. For example, in gasoline markets ethanol mixing is deemed by some to be a negative (e.g., lower energy density). Other types of higher order fuels do not have these same problems and are included into fuel mixtures without these same negative limitations. In addition, some upgraded ethanol products and feedstocks could be utilized in a variety of other industries and applications, including efficiently upgraded feedstocks such as ethanol that form higher value products that can be utilized as replacements (in whole or in part) from fossil derived materials. Hence a need exists to cheaply and efficiently upgrade ethanol to form other types of materials. The present application contains developments that meet these needs.

Generation of C$_5$+ ketones has always been a challenge to be able to reduce the number of reaction steps and to complete in an economically viable manner. Selectively generating C$_5$+ ketones can be useful in the area of fine chemical synthesis and this can also be used in a gasoline blend as an octane booster while maintaining high energy density. We have developed a method in which were able to generate C$_5$+ ketones from ethanol with very high selectivity.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY

The present disclosure provides methods, systems and catalysts for converting an alcohol containing feedstock to an upgraded material in a single catalyst bed. In one instance, the method includes the steps of introducing the feedstock to a catalyst under preselected conditions to obtain an intermediate, and condensing the intermediate through an aldol condensation reaction to yield a product containing an upgraded material. In one instance ethanol is included in the feedstock. In other examples, the catalyst is a mixed metal oxide catalyst, including one that includes $ZrO_2$—ZnO with 0.05 wt % PdO as promoter. In another example the mixed metals catalyst is CuO—MgO—$Al_2O_3$. The upgraded material is typically a C$_5$+ ketone(s) or alcohol(s). Conditions for processing can include a temperature between 300-400° C. and a pressure of atmospheric-500 psig. Examples of materials that could be obtained include 2-pentanone, 2-heptanone, 4-heptanone and 2-nonanone.

In one arrangement a method for converting an ethanol containing feedstock to an upgraded material in a single catalyst bed includes the steps of: introducing the feedstock to a mixed metal oxide catalyst under a set of preselected conditions to obtain an intermediate; and condensing the intermediate through an aldol condensation reaction to yield a product containing a C$_5$+ ketone(s) or alcohol(s). In some specific cases the mixed metal oxide catalyst is $ZrO_2$—ZnO with 0.05 wt % Pd promoter. In other cases the mixed metals catalyst is CuO—MgO—$Al_2O_3$. The catalyst could comprise between 25-75 wt % $ZrO_2$, between 25-75 wt % ZnO and between 0.05-0.5 wt % Pd. Example conditions under which the processing could take place include exposing the materials to a temperature between 300-400° C. and a pressure between atmospheric-500 psig. The resulting C$_5$+ ketone(s) or alcohol(s) could include product materials such as 2-pentanone, 2-heptanone, 4-heptanone and 2-nonanone or 2-pentanol, 2-heptanol, 4-heptanol and 2-nonanol. This arrangement allows for a simplified and efficient production of specified fuels and chemicals and can serve as a front step to a simplified ethanol to fuel conversion without the use of additional hydrogen, with the efficient use of oxygen and carbon.

Various additional advantages and novel features of the present disclosure are described herein and will become further readily apparent to those skilled in this art from the following detailed description. As will be realized, the disclosure is capable of modification in various respects without departing from the disclosure. Accordingly, the drawings and description of the preferred embodiment set forth hereafter are to be regarded as illustrative in nature, and not as restrictive.

BRIEF DESCRIPTION OF THE DRAWINGS

FIGS. 3A-3G show the results of various forms of testing obtained on various examples.

DETAILED DESCRIPTION

As described in detail below in one embodiment a process is provided wherein conversion of ethanol to $C_5+$ ketones in one single catalytic step (mixed metal oxide) or to $C_5+$ alcohols in dual catalytic step (mixed metal oxide followed by mild hydrogenation catalyst) with overall carbon efficiency greater than 83% at mild operating conditions (temperature between 300-400° C. and a pressure of atmospheric-500 psig) was performed. The results of this particular embodiment demonstrated that at 370° C. and 300 psig, there is 80% selectivity to $C_5$ to $C_{11}$ ketones. 2-pentanone, 2-heptanone, 4-heptanone and 4-nonanone are the major products. These materials can then be distilled and sold as ketones to be used as value added chemicals. For example; some 2-ketones sell for as much as $20/kg based on Aldrich prices. Further modifications have shown reductions in the complexity of the processes, improving the overall selectivity and yield to higher ketones, improve catalyst lifetime, and reduce material and catalyst synthesis costs. Operating at higher temperature (>370° C.) will result in producing ketones with higher carbon number (higher molecular weight compounds) and cyclic compounds (e.g., phenolics and aromatics).

This methodology to upgrade ethanol using advanced carbon to carbon (C—C) coupling chemistry to produce a broad range of fuels and chemicals with very high carbon efficiency makes possible a variety of new applications. It is envisioned that in downstream applications this technology can be integrated to existing ethanol plants as an add-on process where fuels and commodity chemicals are produced in tandem and can also be alternatively configured and embodied as well.

Figure 1:
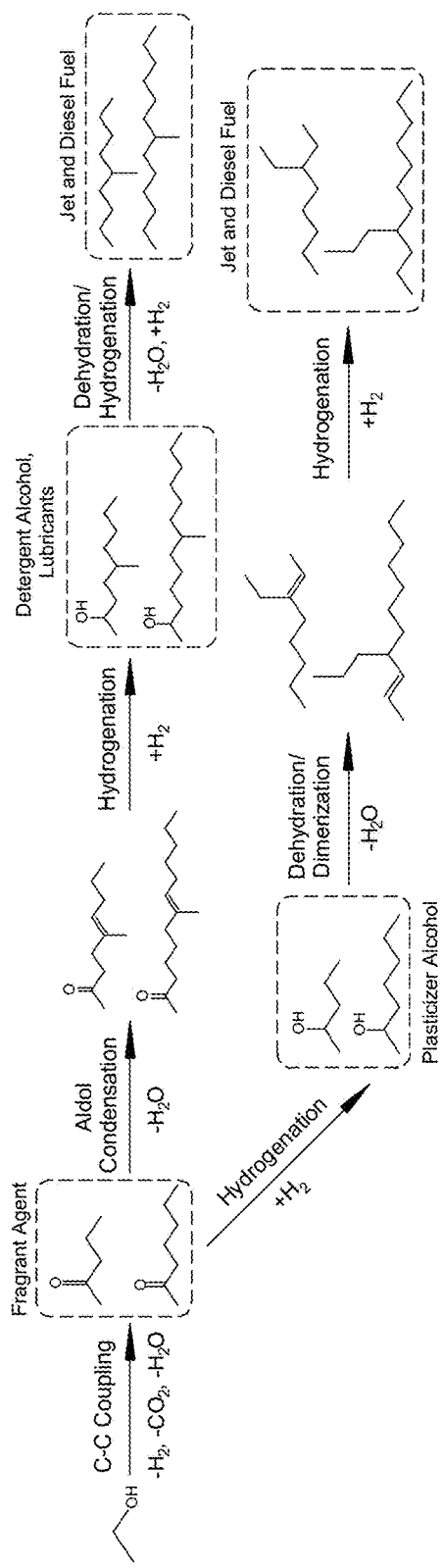
FIG. 1 show examples of different chemistries involved in producing infrastructure compatible fuels and high value co-products through an ethanol to higher ketones pathway by utilizing existing chemistries such as aldol condensation, dehydration and hydrogenation.

FIG. 1 depicts the different chemistries involved in producing infrastructure compatible fuels and high value co-products through an ethanol to higher ketones pathway by utilizing existing chemistries such as aldol condensation, dehydration and hydrogenation. As shown in FIG. 1, in one step ethanol is converted to $C_{5-11}$ ketones that can be used as food additives, fragrant agents, and solvents. The ketones mixture can be separated by simply distilling the ketones with different carbon numbers and utilized without any further downstream processing. These ketones can also be used as building blocks for other chemicals and fuels.

Further hydrogenations of these ketones generate alcohols in the oxo/plasticizer alcohols range. Using dehydration-dimerization-hydrogenation step the plasticizer range alcohol can be converted to jet fuel and diesel. The other option is to use self-aldol condensation of the $C_5+$ ketones followed by a hydrogenation step to generate detergent alcohols and lubricants from the $C_{5-11}$ ketones. These higher alcohols can also be converted to jet fuel and diesel via a simple dehydration-hydrogenation step. These are only a few of the potential routes that can be used to convert ethanol to valuable co-products and fuels via the demonstrated higher ketones pathway.

Due to the reactive nature and the higher carbon chain length ($C_{5-11}$) of the ketones generated from ethanol, simple ethanol to ketone processing provides significant potential opportunity and the versatility to produce various different valuable co-products of interest including fuels that can potentially help replace the whole barrel of crude oil. This higher ketones pathway would also enable a variety of newer opportunities that are otherwise not available via renewable means.

Figure 2:
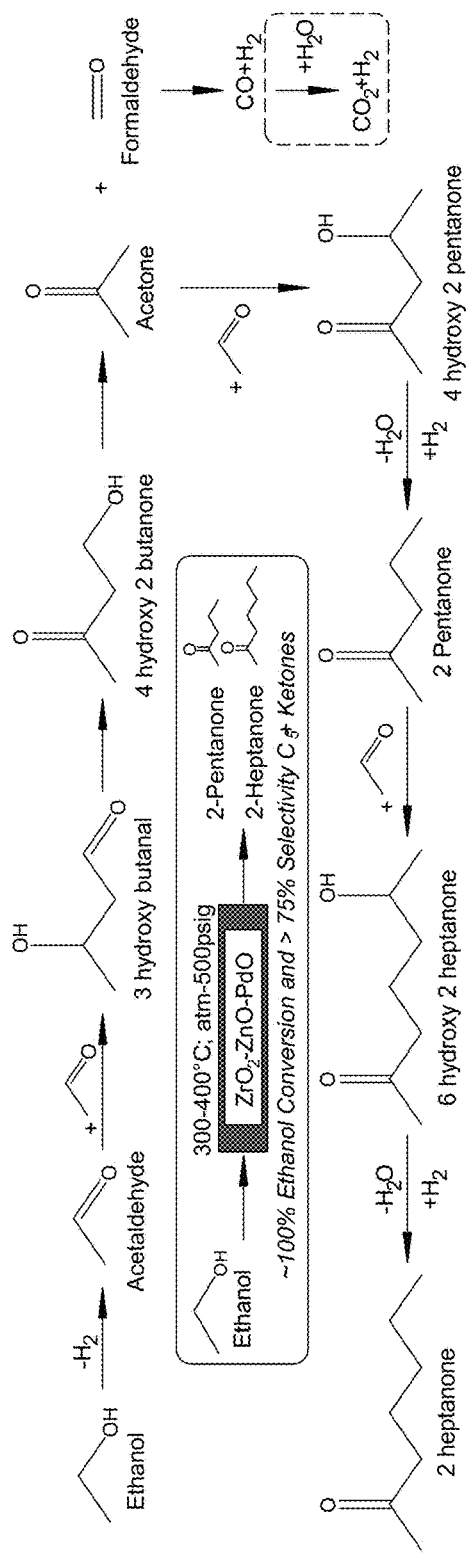
FIG. 2 shows the proposed chemistry, the process conditions and the major compounds generated from the ethanol to higher ketones process.

The present disclosure provides a description of recent work that has demonstrated a novel pathway to selectively convert ethanol to $C_5+$ ketones with minimal loss of carbon over a low cost multi-functional mixed oxide catalyst ($ZrO_2$—ZnO) with >70% yield to $C_5+$ ketones. FIG. 2 shows the proposed chemistry, the process conditions and the major compounds generated from the ethanol to higher ketones process. In such an arrangement, a feedstock containing ethanol is passed over a mixed oxide catalyst having a promoter at temperatures between 300° C. and 400° C., pressure between atmospheric and 500 psig, and at a weight hourly space velocity between 0.1 hour$^{-1}$ and 1 hour$^{-1}$. Under these conditions the ethanol dehydrogenates to form acetaldehyde. Molecules of acetaldehyde then condense to form hydroxybutanal which then isomerizes (intermolecular hydride shift) to form hydroxybutanone, followed by retro-aldol reaction to form acetone and formaldehyde. Once acetone is formed it continuously reacts with acetaldehyde via cross aldol condensation to generate $C_5+$ ketones such as 2-pentanone and 2-heptanone (examples of the desired $C_5+$ end products). The only step where carbon loss occurs is via the decomposition of formaldehyde during acetone formation.

The uniqueness of this chemistry is the condensation of acetone with acetaldehyde to form 2-pentanone rather than the self-condensation between acetone to form diacetone alcohol and mesityl oxide. These results are due to the unique combination of metal promoted mixed oxide catalyst providing the required acid, base and hydrogenation/dehydrogenation sites and help to improve the final product yield and reduce the overall carbon loss. Since the product chain growth occurs via the addition of acetaldehyde to the higher ketones rather than acetone (cross aldol condensation), and the carbon loss occurs only in the acetone formation, leading to increased carbon efficiency with an increase in the carbon number of the ketones generated. For example, from ethanol the theoretical carbon efficiency for 2-pentanone formation is ~83% and for nonanone formation is ~90%. This also provides an opportunity to fine tune the chemistry to push towards $C_9+$ ketones and it further improves the carbon efficiency, product yield and provides the potential to produce oxygenated value-added products.

The cascading nature of the chemistry in converting the ethanol to higher ketones requires a multi-functional catalytic system. The catalysts of interest are those containing both acidic and basic properties. For example, mixed oxide materials such as $ZrO_2$—ZnO, MgO—$Al_2O_3$, and MgO—$SiO_2$, along with promoter materials such as Ag, Pt, Pd, Cu, and Ni, are envisioned as the catalysts of interest. In general, bulk mixed-oxides are widely employed in industry as heterogeneous catalysts for selective oxidation, so the cost of the materials as well as the catalyst synthesis should be competitive.

In some applications ethanol conversion to generate $C_5+$ ketones over multi-functional catalyst(s) in a fixed bed reactor at 100% ethanol conversion and selectivity to ketones ≥80% can be completed under specified operating parameters such as temperature, pressure and space velocities. In other applications $C_5+$ ketone hydrogenation to produce alcohols (e.g., plasticizer/oxo-alcohol) can be performed to achieve >90% conversion of the ketones with >90% selectivity to the alcohols and complete the initial proof of concept integrated process to (jet) fuel (Q1). Some other applications of the present invention include self-aldol condensation of the $C_5+$ ketone compounds followed by the hydrogenation to demonstrate the detergent and lubricant range alcohols, the conversion of ethanol to fuels and chemicals in a biorefinery process via the renewable ethanol→$C_{5-15}$ ketones→$C_{5-15}$ alcohols→jet and diesel fuel process with the overall carbon efficiency of ≥30% from ethanol to fuels and co-products.

The following examples provide information regarding particular embodiments and examples. These examples are meant to be illustrative only and not limiting. In one example zirconyl nitrate solution [$Zr(NO_3)_4$] and Zinc nitrate [$Zr(NO_3)_4$] were dissolved in deionized (DI) water and heated at 75° C. The composition between the $Zr(NO_3)_4$ and $Zr(NO_3)_4$ varies based on the final catalyst composition. At this state the pH of the solution remains around 1. Then potassium hydroxide was added to the solution until the pH of the solution reached around 10.5. This solution was stirred continuously and aged for approximately 22 h at 75° C. The aged material was filtered and washed with DI water at 85° C. until the dissolved solids in the wash solution reached approximately 50 ppm. Then the washed material was dried overnight at 90° C. The dried material was crushed to fine powder and pelletized at 15,000 lbs pressure and sieved between 35 and 100 mesh. The sieved material was then calcined at 450° C. for 3 h in a furnace. This material is denoted as the base ($ZrO_2$—ZnO) mixed oxide material. This base mixed oxide material was then impregnated with various metals such as palladium (between 0.05 wt % and 0.5 wt %), silver (0.5 wt %), copper (1 wt %), and platinum (0.1 wt %). The impregnated material was then dried for about 2 h and calcined again at 450° C. for 3 h.

Various catalyst testing experiments were conducted on a down flow gas-phase reactor arrangement. The catalyst of interest was placed in the middle of the reactor tube (isothermal zone) and heated using a tube furnace. Ethanol and carrier gas nitrogen ($N_2$) was fed from the top of the reactor. The liquid product samples were collected in the bottom of the reactor in a cold trap (ice bath) arrangement. Later the collected liquid products were analyzed by gas chromatography-flame ionization detector and by gas chromatography/mass spectrometry. The non-condensable gases from the cold trap passed through the flow meter and were analyzed by gas chromatography-thermal conductivity detector. The gas samples were collected on an interval of every one hour and the liquid samples were collected every 24 h. The catalysts were tested at temperature between 300° C. and 400° C., pressure between atmospheric and 500 psig, and weight hourly space velocity between 0.1 $hour^{-1}$ and 1 $hour^{-1}$. The results of various forms of testing obtained on these items is shown in FIGS. 3A-3G).

Developing technologies that fit the (ethanol) biorefinery concept to generate fuels and chemicals in tandem with flexibility, based on the market demand via simple and economical pathways is valuable. One of the major advantages of ethanol is it can be made from a wide variety of feed sources such as cellulosic biomass, algae, wet waste, coal, biogas and flue gas. In addition, $C_4$ compounds such as 1-butanol and 1-3 butadiene and the production of jet fuel have generated significant research interest recently. 1-butanol has great flexibility to be used as a fuel blendstock or intermediate for fuels and chemicals and 1-3 butadiene is an important chemical monomer in the production of synthetic rubber. The ethanol to fuels and co-products via higher ketones pathway will be complimentary to the currently known ethanol conversion pathways and beneficial to realize the biorefinery concept through developing new renewable technologies to produce fuels and high value co-products such as oxo-alcohols, plasticizer alcohols, detergent alcohols, lubricants, food aroma and fragrant agents that are otherwise produced by fossil resources.

Figure 4:
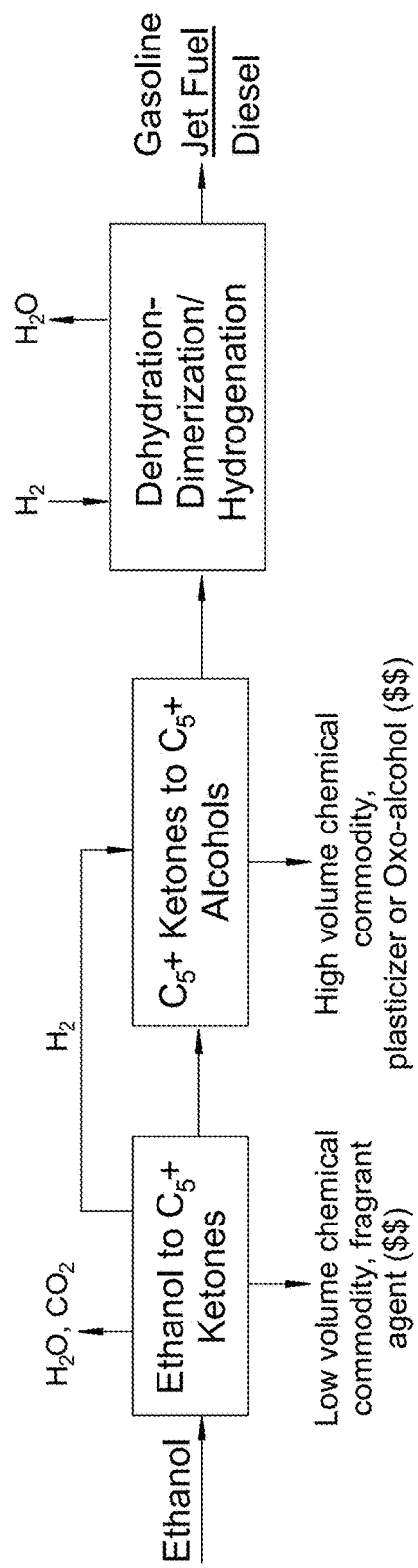
FIG. 4 shows the process flow diagram for the proposed ethanol to (jet) fuel and co-products process.

FIG. 4 shows the process flow diagram of the ethanol to (jet) fuel processes via ethanol to $C_5+$ ketones process. This configuration and arrangement provides a variety of advantages over the other ethanol to (jet) fuel technologies. These include: various different potential high value co-product insertion points at different stages of the process; $C_5+$ ketones as fragrant and aroma agent, $C_5+$ alcohols as plasticizer/oxo-alcohols; $C_5+$ ketones are intermediates for detergent alcohols and other co-products; provides potential flexibility between co-products and fuels based on the market needs; oxygen containing co-products improves the overall biomass to final products and fuels yield; no recycle required (~100% conversion chemistries); reduces the capital cost and operational cost; potentially reduced number of unit ops for final fuel generation via process intensification; overall carbon loss via $CO_2$ is potentially below 10 percent to fuels and co-products; and most of the hydrogen required will be recovered from the process itself.

Additional objects, advantages and novel features of the present invention are described herein and will become further readily apparent to those skilled in this art from the following detailed description. In the preceding and following descriptions it has been shown and described only the preferred embodiment of the invention, by way of illustration of the best mode contemplated for carrying out the invention. As will be realized, the invention is capable of modification in various respects without departing from the invention. Accordingly, the drawings and description of the preferred embodiment set forth herein are to be regarded as illustrative in nature, and not as restrictive.

What is claimed is:

1. A method for converting an ethanol containing feedstock to an upgraded material in a single catalyst bed the method comprising the steps of:
    introducing the feedstock to a mixed metal oxide catalyst comprising ZrO2-ZnO with 0.05 wt % Pd as promoter under preselected conditions to obtain an intermediate; and condensing the intermediate through an aldol condensation reaction to yield a product containing an upgraded material.

2. The method of claim 1 wherein the upgraded material is a $C_5+$ ketone(s) or alcohol(s).

3. The method of claim 1 wherein the preselected conditions include a temperature between 300-400° C. and a pressure of atmospheric-500 psig.

4. The method of claim 2 wherein the upgraded material is selected from the group consisting of 2-pentanone, 2-heptanone, 4-heptanone and 2-nonanone.

5. A method for converting an ethanol containing feedstock to an upgraded material in a single catalyst bed the method comprising the steps of:
    introducing the feedstock to a ZrO2-ZnO with 0.05 wt % Pd promoter catalyst under a preselected conditions to obtain an intermediate; and condensing the intermediate through an aldol condensation reaction to yield a product containing a $C_5+$ ketone(s) or alcohol(s).

6. The method of claim 5 wherein the preselected conditions include a temperature between 300-400° C. and a pressure of atmospheric-500 psig.

7. The method of claim 5 wherein the $C_5+$ ketone(s) or alcohol(s) is selected from the group consisting of 2-pentanone, 2-heptanone, 4-heptanone and 2-nonanone.

8. A method for converting an ethanol alcohol containing feedstock to an upgraded material in a single catalyst bed the method comprising the steps of:
   introducing the feedstock to a CuO—MgO—Al2O3 catalyst under preselected conditions to obtain an intermediate; and condensing the intermediate through an aldol condensation reaction to yield a product containing an upgraded material.

9. The method of claim 8 wherein the upgraded material is a C5+ ketone(s) or alcohol(s).

10. The method of claim 8 wherein the preselected conditions include a temperature between 300-400° C. and a pressure of atmospheric-500 psig.

11. The method of claim 9 wherein the upgraded material is selected from the group consisting of 2-pentanone, 2-heptanone, 4-heptanone and 2-nonanone.

12. A method for converting an ethanol containing feedstock to an upgraded material in a single catalyst bed the method comprising the steps of:
   introducing the feedstock to a CuO—MgO—$Al_2O_3$ catalyst under a preselected conditions to obtain an intermediate; and condensing the intermediate through an aldol condensation reaction to yield a product containing a C5+ ketone(s) or alcohol(s).

13. The method of claim 12 wherein the preselected conditions include a temperature between 300-400° C. and a pressure of atmospheric-500 psig.

14. The method of claim 12 wherein the C5+ ketone(s) or alcohol(s) is selected from the group consisting of 2-pentanone, 2-heptanone, 4-heptanone and 2-nonanone.

* * * * *